(12) United States Patent
Rezach

(10) Patent No.: US 7,717,921 B2
(45) Date of Patent: May 18, 2010

(54) INSTRUMENTS AND METHODS FOR DELIVERING MULTIPLE IMPLANTS IN A SURGICAL PROCEDURE

(75) Inventor: W. Alan Rezach, Atoka, TN (US)

(73) Assignee: Warsaw Orthopedic, Inc.

( * ) Notice: Subject to any disclaimer, the term of this patent is extended or adjusted under 35 U.S.C. 154(b) by 1244 days.

(21) Appl. No.: 11/253,880

(22) Filed: Oct. 19, 2005

(65) Prior Publication Data

US 2007/0088363 A1   Apr. 19, 2007

(51) Int. Cl.
*A61B 17/58* (2006.01)

(52) U.S. Cl. .............. 606/99; 606/86 A; 606/86 B; 279/82

(58) Field of Classification Search .......... 606/99, 606/100, 86 R, 914, 915, 916, 86 A, 86 B; 81/451, 13, 177.85; 221/292, 289, 298, 312 A; 279/74, 75, 82
See application file for complete search history.

(56) References Cited

U.S. PATENT DOCUMENTS

| | | | |
|---|---|---|---|
| 1,537,929 A * | 5/1925 | Henry ................ 81/125 |
| 2,247,500 A | 7/1941 | Hutchison |
| 3,073,610 A * | 1/1963 | MacKinder et al. ........ 279/2.17 |
| 3,300,090 A * | 1/1967 | Carden ................ 221/281 |
| 4,198,066 A * | 4/1980 | Deprez et al. .............. 279/2.03 |
| 4,811,647 A | 3/1989 | Lindamood |
| 4,958,873 A * | 9/1990 | Akagawa ................ 294/93 |
| 4,963,144 A | 10/1990 | Huene |
| 5,437,211 A | 8/1995 | Wolfe |
| 5,445,641 A | 8/1995 | Frigg et al. |
| 5,590,574 A | 1/1997 | Lide |
| 5,649,931 A | 7/1997 | Bryant et al. |
| 5,735,854 A | 4/1998 | Caron et al. |
| 5,791,207 A | 8/1998 | Ahdoot |
| 5,941,885 A | 8/1999 | Jackson |
| 6,112,944 A * | 9/2000 | Van Hoorn et al. ......... 221/298 |
| 6,129,730 A | 10/2000 | Bono et al. |
| 6,132,435 A | 10/2000 | Young |
| 6,224,596 B1 | 5/2001 | Jackson |
| 6,273,893 B1 | 8/2001 | McAllen, III et al. |
| 6,283,973 B1 | 9/2001 | Hubbard et al. |
| 6,328,746 B1 | 12/2001 | Gambale |
| 6,634,261 B1 | 10/2003 | Griffin |
| 7,147,641 B2 | 12/2006 | Chen |
| 7,240,588 B1 | 7/2007 | Rinner |
| 7,451,893 B2 * | 11/2008 | Martin ................ 221/298 |
| 2004/0243139 A1 | 12/2004 | Lewis et al. |
| 2005/0149031 A1 | 7/2005 | Ciccone et al. |
| 2005/0203530 A1 | 9/2005 | Oribe et al. |
| 2006/0027592 A1 * | 2/2006 | Flamingo et al. ........... 221/103 |
| 2007/0276403 A1 | 11/2007 | Franks et al. |
| 2008/0255576 A1 | 10/2008 | Protopsaltis |

FOREIGN PATENT DOCUMENTS

| | | |
|---|---|---|
| DE | 298 16 215 U1 | 11/1998 |
| FR | 668 187 | 10/1929 |
| GB | 2 355 505 A | 4/2001 |
| WO | WO 94/12111 | 6/1994 |
| WO | WO 02/45585 A2 | 6/2002 |

* cited by examiner

*Primary Examiner*—Eduardo C Robert
*Assistant Examiner*—Jan Christopher Merene

(57) ABSTRACT

Instruments and methods are provided for delivering multiple implants to locations for implantation in a patient without requiring a second implant to be loaded onto or engaged to the delivery instrument after delivery of a first implant.

14 Claims, 4 Drawing Sheets

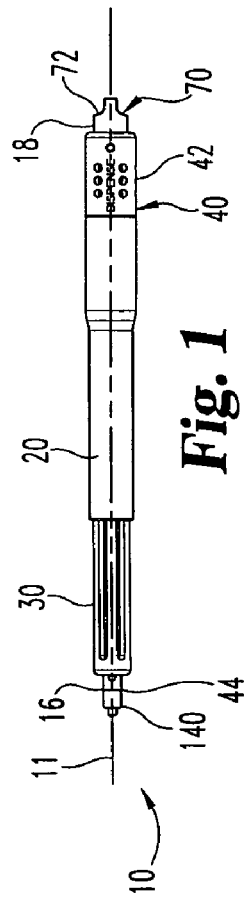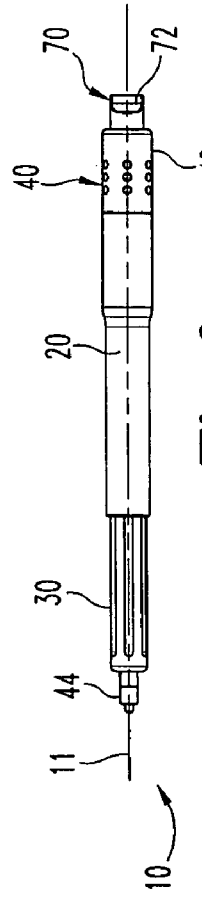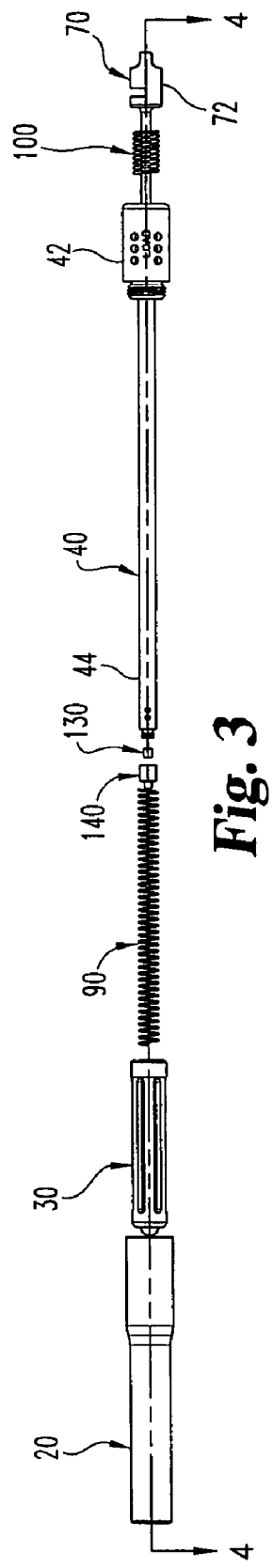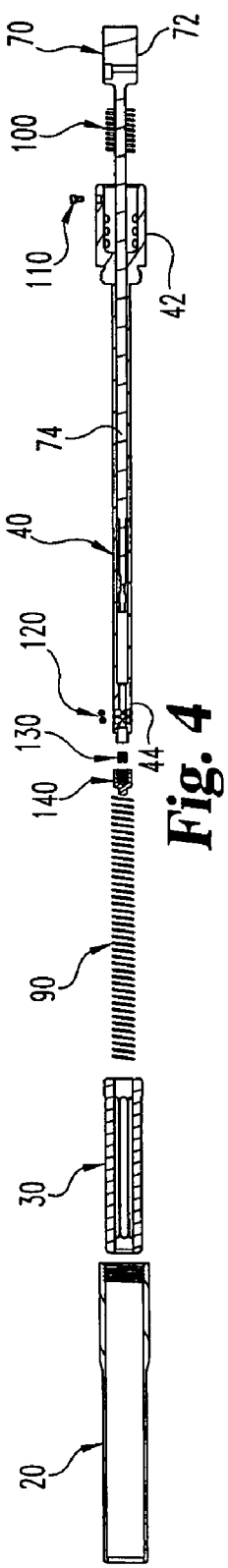

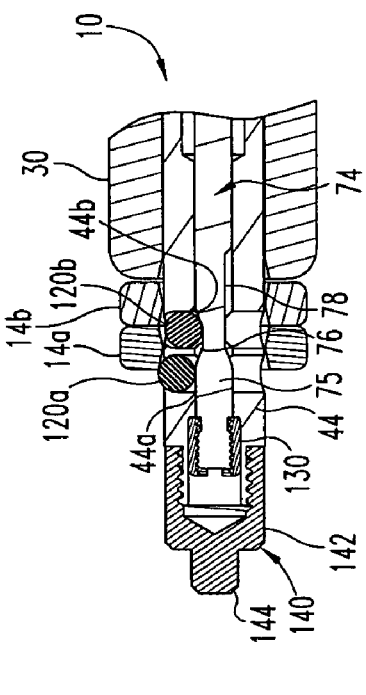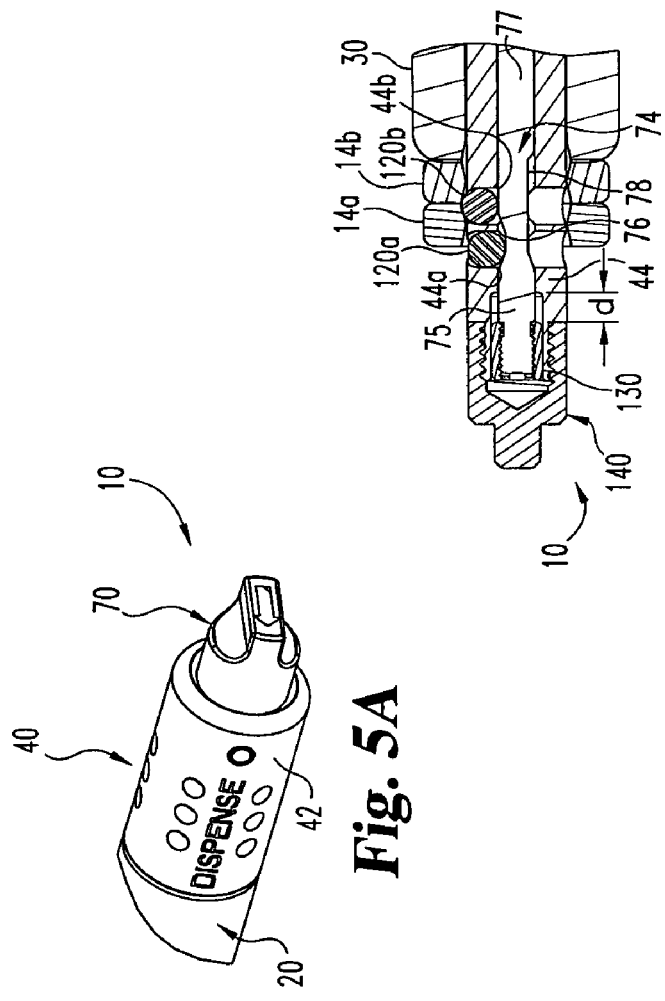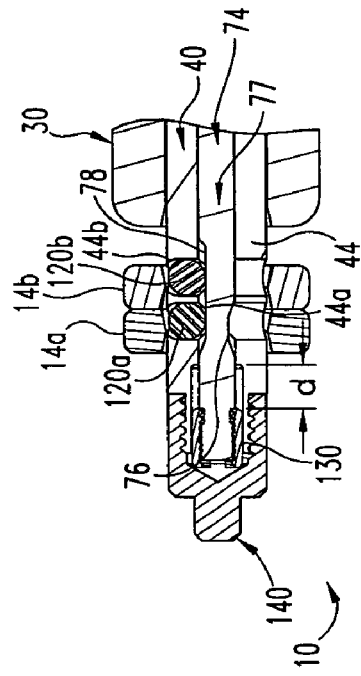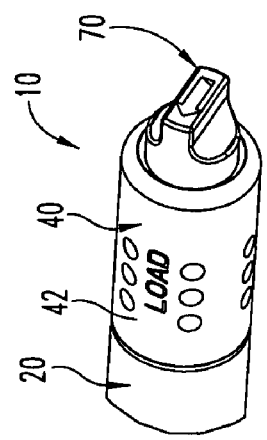

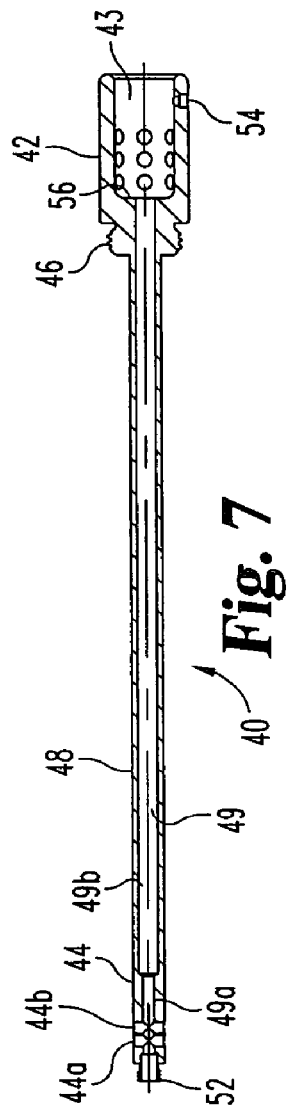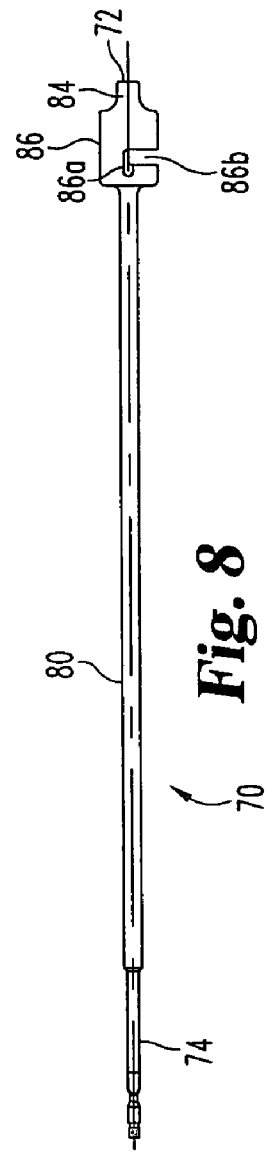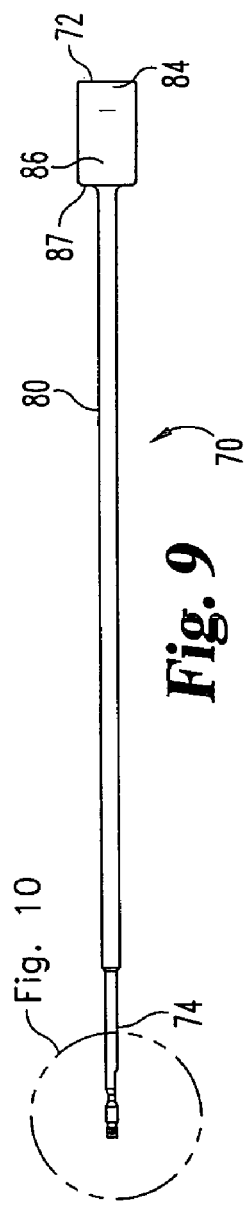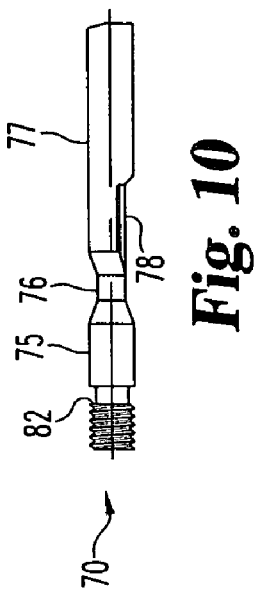

US 7,717,921 B2

INSTRUMENTS AND METHODS FOR DELIVERING MULTIPLE IMPLANTS IN A SURGICAL PROCEDURE

BACKGROUND

Various types of devices and systems have been used for positioning implants into a patient in surgical procedures. Spinal stabilization systems have employed plating systems, rods, anchors, fusions devices, artificial discs, and other implants along or in the spinal column for rigid, dynamic, and semi-rigid spinal stabilization procedures. Such systems often include multiple implant members that must be engaged for the system to be properly installed. There remains a need for instruments and methods for delivering multiple implants to the implantation location while minimizing the time and complexity associated with handling and positioning such implants during surgery.

SUMMARY

According to one aspect, an instrument for delivering multiple implants to at least one surgical location in a patient includes a mounting member, a retaining mechanism housed in the mounting member, and an actuator coupled to the mounting member. The mounting member includes an elongate tubular portion extending between a distal mounting portion for receiving multiple implants therealong and a proximal end member. The retaining mechanism is movable between a retaining position for retaining the implants along the mounting portion and a dispensing position allowing a distal-most implant on the mounting portion to move distally along the mounting portion for delivery to the at least one surgical location. The actuator includes a proximal engaging end adjacent the proximal end member of the mounting member. The actuator extends from the proximal engaging end through the tubular portion to an actuating end along the mounting portion. The actuator includes a first axial position with the actuating end positioning the retaining mechanism in the retaining position. The actuator is movable in the mounting member to a second axial position with the actuating end positioning the retaining mechanism in the dispensing position.

According to another aspect, an instrument for delivering multiple implants to at least one surgical location in a patient includes a mounting member, an actuator in the mounting member, and distal and proximal retaining members in the mounting member in contact with the actuator. The mounting member includes an elongate tubular portion extending between a distal mounting portion for receiving multiple implants therealong and a proximal end member. The actuator includes a distal actuating end in the tubular portion of the mounting member and a proximal engaging end received in the end member of the mounting member. The actuator has a first rotational alignment relative to the mounting member wherein the actuator is axially movable in the mounting member between a retaining position and a dispensing position. In the retaining position the distal retaining member projects outwardly from the mounting portion and contacts a distal-most implant to axially retain the multiple implants on the mounting portion and the proximal retaining member is recessed in the mounting portion. In the dispensing position the distal retaining member is recessed into the mounting portion to permit the distal-most implant to advance distally along the mounting portion for implantation and the proximal retaining member projects outwardly from the mounting portion to contact a second implant proximal of the distal-most implant to axially retain the second implant on the mounting portion.

In another aspect, a surgical system includes a delivery instrument and multiple implants along the delivery instrument. The delivery instrument includes an elongated mounting member having a distal mounting portion and a proximal end member, an actuator in the mounting member including an actuating end in the mounting portion and a proximal engaging end extending proximally from the proximal end member of the mounting member, and a retaining mechanism in the mounting member movable upon axial displacement of the actuator in the mounting member between a retaining position and a dispensing position. The plurality of implants positioned about the mounting portion include a distal-most implant in contact with the retaining mechanism in the retaining position and a proximal most implant in contact with a biasing member biasing the multiple implants distally into contact with the retaining mechanism.

In yet another aspect, a method for delivering multiple implants to an implantation location comprises: positioning a distal end of a delivery instrument at a first implantation location, the delivery instrument including a first distal-most implant and at least one second implant proximal the first implant positioned about and retained on the delivery instrument; distally advancing the first implant along the delivery instrument for implantation at the implantation location while simultaneously retaining the at least one second implant on the delivery instrument with the delivery instrument; positioning the distal end of the delivery instrument adjacent a second implantation location; and distally advancing the at least one second implant along the delivery instrument for implantation at the second implantation location.

These and other aspects will also be apparent from the following description.

BRIEF DESCRIPTION OF THE DRAWINGS

FIG. 1 is an elevation view of a delivery instrument for delivering multiple implants in a surgical implantation location.

FIG. 2 is an elevation view of the delivery instrument of FIG. 1 rotated 90 degrees about its longitudinal axis from its FIG. 1 positioning.

FIG. 3 is an exploded view of the delivery instrument of FIG. 1.

FIG. 4 is a section view along line 4-4 of FIG. 3.

FIG. 5A is a perspective view of a proximal end of the delivery instrument in a dispensing orientation.

FIG. 5B is a sectional view of a distal portion of the delivery instrument with the delivery instrument in the dispensing orientation and the actuator and retaining mechanism in a retaining position.

FIG. 5C is a sectional view of the distal portion of the delivery instrument of FIG. 5B with the delivery instrument in the dispensing orientation and the actuator and retaining mechanism in a dispense position.

FIG. 6A is a perspective view of the proximal end of the delivery instrument in a loading orientation.

FIG. 6B is a sectional view of the distal portion of the delivery instrument with the actuator and retaining mechanism in the loading orientation.

FIG. 7 is a longitudinal section view of a mounting member of the delivery instrument of FIG. 1.

FIG. 8 is an elevation view of an actuator of the delivery instrument of FIG. 1.

FIG. 9 is an elevation view of the actuator of FIG. 8 rotated 90 degrees about its longitudinal axis from its FIG. 8 orientation.

FIG. 10 is an enlarged view of a distal portion of the actuator of FIG. 9.

DESCRIPTION OF THE ILLUSTRATED EMBODIMENTS

Figure 11:
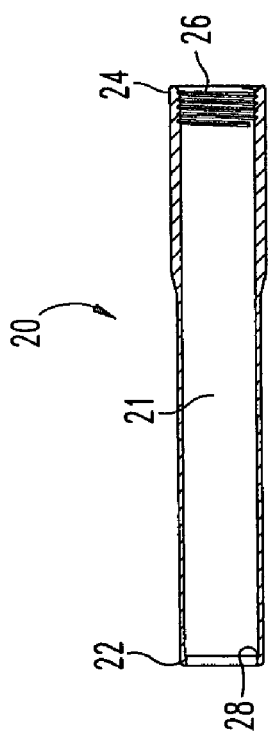
FIG. 11 is a longitudinal section view of a housing of the delivery instrument of FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Positioning of multiple implants during a surgical procedure without withdrawing or re-loading the delivery instrument with an implant is facilitated by a delivery instrument that includes a mounting member with multiple implants positioned axially therealong. The multiple implants are axially retained on the mounting portion until positioned adjacent an implantation location. The instrument can be actuated to deliver the distal-most implant from the distal end of the delivery instrument to the implantation location while the next most distal implant is axially retained on the mounting portion. The delivery instrument can then be re-positioned, or maintained in the same position, for delivery of the second implant from the distal end by actuating the delivery instrument. The process can be repeated until all required implants have been delivered or until it is necessary to re-load the delivery instrument with additional implants.

The delivery instrument can include an actuator that is operable at the proximal end of the delivery instrument to effect delivery and retention of the implants along the distal mounting portion of the delivery instrument. In one embodiment, the actuator includes a dispensing orientation that provides a push-button type control to dispense the implants from the delivery instrument. The actuator is moveable to a loading orientation that allows multiple implants to be loaded about the mounting portion from the distal end of the instrument. After loading of the implants, the actuator is movable to the dispensing orientation where the implants are retained on the mounting portion until the actuator is depressed by the user to deliver the distal-most implant.

The implantation location can be an implant engageable to bony structure of the patient, such as a spinal plate, a bone screw, a clamp, an interbody device, or any other construct. In one specific technique, the implantation location is a proximally extending post of a bone screw, and the implant is a washer that is positionable about the post. Multiple implants can be delivered to the same location, or to multiple locations in the patient. The washers can facilitate securement of a plate or rod to the bone screw post in a desired position therewith.

In FIGS. 1-4 there is shown a delivery instrument 10 extending along a longitudinal axis 11 between a distal mounting end 16 about which multiple implants can be mounted and a proximal actuating end 18 to effectuate delivery of the implants from distal mounting end 16. In the illustrated embodiment delivery instrument 10 includes a housing 20 to which a mounting member 40 is mounted. Mounting member 40 extends through housing 20 between a proximal end member 42 proximal of housing 20 and a distal mounting portion 44 distal of housing 20. Multiple implants 14 (FIG. 5) can be mounted about distal shaft portion 44 and retained thereon with a retaining mechanism 120. Retaining mechanism 120 is movable with an actuator 70 between a retaining position to retain the implants on mounting portion 44 and a dispensing position where the distal-most implant is movable axially along mounting portion 44 for delivery from the distal end of delivery instrument 10.

Actuator 70 extends through mounting member 40 between a proximal user engaging end 72 and a distal actuating end 74 in mounting member 40. Engaging end 72 can be manipulated by the user to selectively move actuator 70 in mounting member 40 so that actuating end 74 selectively deploys and recesses retaining mechanism 120 between the retaining position and the dispensing position.

Delivery instrument 10 further includes a piston member 30 movably received in housing 20 and about mounting member 40 that is distally biased along mounting member 40 and into contact with the implants along mounting portion 44. Piston member 30 is axially restrained in the distal direction by a distally oriented outer lip about piston member 30 adjacent its proximal end that contacts with a proximally oriented inner lip about housing 20 adjacent its distal end.

In the dispensing orientation actuator 70 is proximally biased in mounting member 40 when in a first rotational alignment therewith so that it is normally in a retaining position. The user can move actuator 70 axially by pressing engaging end 72 distally in mounting member 40 to a dispense position. In the dispensing position actuating end 74 is configured and positioned to manipulate retaining mechanism 120 so that distal-most implant is movable distally along mounting portion 44 for delivery therefrom while the next most distal implant is axially retained on mounting portion 44 by retaining mechanism 120. The distally directed force supplied by piston member 30 can assist in advancing the implants distally along mounting portion 44, although embodiments without piston member are contemplated where the implants advance solely due to gravity.

In the loading orientation, actuator 70 can further be configured so that when it is in a second rotational alignment with mounting member 40 the retaining mechanism 120 is positioned to allow implants to be axially loaded into mounting portion 44. In this loading position, actuating end 74 is configured and position relative to retaining mechanism 120 so that it is recessed in mounting member 40, allowing implants to be loaded about mounting member 40 without interference from retaining mechanism 120. Piston member 30 can be manually restrained in a proximal position about mounting member 40 as the implants are loaded along mounting portion 44. When actuator 70 is returned to its first rotational alignment in mounting member 40 in the dispensing orientation, piston 30 can be released to contact the proximal most implant and bias the multiple implants distally into contact with retaining mechanism 120 in its retaining position.

Further details of operation of actuator 70 to dispense and load implants about mounting member 40 are shown in FIGS. 5A-6B. In FIG. 5A, actuator 70 is positioned in the dispensing orientation relative to mounting member 40. An arrow or other indicator can be provided on the proximal end of actuator 70 that can align with the word "DISPENSE" or some other indicator on the side of mounting member 40 to provide the user an indication that delivery instrument 10 is rotationally aligned with mounting member 40 in an orientation that allows actuator 70 to be axially moved from the retaining position to the dispensing position. When in this first rotational alignment, the distal actuating end 74 is positioned in a first axial position relative to retaining members 120*a*, 120*b* of retaining mechanism 120, as shown in FIG. 5B. In this first axial position, actuating end 74 contacts retaining members 120*a*, 120*b* to maintain retaining members 120*a*, 120*b* in the retaining position. In the illustrated embodiment, retaining members 120*a*, 120*b* are ball-shaped members that are sized relative to detents 44*a*, 44*b* to project therefrom when bottomed out in the respective detents 44*a*, 44*b*, but are too large to pass through detents 44*a*, 44*b*.

In the retaining position of FIG. 5B, proximal retaining member 120*b* is aligned with a retaining member recess 76 in actuating end 74 so that it can recess into proximal detent 44*b* of mounting portion 44 and not project outwardly from the outer surface of mounting portion 44. Distal retaining member 120*a*, on the other hand, is in contact with a distal actuating shaft portion 75 of actuating end 74 and forced into distal detent 44*a* so that distal retaining member 120*a* projects outwardly from the outer surface of mounting portion 44. Distal retaining member 120*a* thus prevents implants 14*a*, 14*b* about mounting portion 44 from sliding distally along mounting portion 44. Implant 14*a* can be located distally of the proximal retaining member 120*b*. The distal end of the second most distal implant 14*b*, however, is located proximally of proximal retaining member 120*b*. Piston member 30 pushes against the proximal-most implant and forces the distal-most implant 14*a* into contact with retaining member 120 and the remaining implants into end-to-end contact with one another along mounting portion 44.

In the retaining position of FIG. 5B, a distal end member 130 of actuator 70 contacts a distal end wall of mounting member 40, maintaining the proximally biased actuator 70 in the retaining position. Actuator 70 can be axially moved toward the dispensing position by axially and distally displacing actuator 70 in mounting member 40, as shown in FIG. 5C, locating actuating end 74 in a second axial position relative to mounting portion 44 and spacing distal end member 130 a distance d from a distally oriented end wall of mounting member 40. In the dispensing position of FIG. 5C, distal retaining member 120*a* is aligned with retaining member recess 76 in actuating end 74 so that it can recess into distal detent 44*a* of mounting portion 44 and not project outwardly from the outer surface of mounting portion 44. Distal implant 14*a* can thus move distally along mounting portion 44 by gravity and/or the bias of piston member 30 for delivery therefrom. Proximal retaining member 120*b*, on the other hand, is in contact with a proximal actuating shaft portion 77 of actuating end 74 and pushed into proximal detent 44*b* sufficiently to project outwardly from the outer surface of mounting portion 44. Proximal retaining member 120*b* thus prevents the next most distal implant 14*b* about mounting portion 44 from sliding distally along mounting portion 44 when the distal-most implant is being delivered.

When the proximal end of actuator 70 is released, it is spring biased proximally to return actuating end 74 to its first axial position and to the retaining position shown in FIG. 5B. The next most distal implant 14*b* moves distally along mounting portion 44 via gravity and/or the bias from piston member 30 to contact distal retaining member 120*a*, while proximal retaining member 120*b* recesses into mounting portion 44. The process can be repeated for each implant 14 to be dispensed from mounting portion 44 of mounting member 40.

FIGS. 6A and 6B show actuator 70 positioned in a second rotational alignment with mounting member 40 in a loading orientation to permit loading of implants onto mounting portion 44 of mounting member 40. In FIG. 6A, the proximal end of actuator 70 is rotated relative to mounting member 40 180 degrees from its orientation in FIGS. 5A-5C. Mounting member 40 can be inscribed with the word "LOAD" or include some other indicator to indicate that actuator 70 is in the loading orientation when the arrow is aligned therewith. In one embodiment, actuator 70 is pressed distally against the proximal bias thereof, and is then rotated to position an alignment pin 110 in a keyed portion of actuator 70. The engagement of alignment pin 110 in the keyed portion of actuator 70 allows alignment pin 110 to maintain actuator 70 in its distally displaced position relative to mounting member 40 without the application of manual pressure at the proximal end of actuator 70 to overcome the proximal bias of actuator 70.

As shown in FIG. 6B, in the loading position distal end member 130 is spaced distance d from the distally oriented end wall of mounting member 40. Actuating end 74 includes an elongated recess 78 that is aligned with detents 44*a*, 44*b*. Elongated recess 78 is configured to permit both retaining members 120*a*, 120*b* to simultaneously recess into mounting member 40, avoiding interference with the loading of implants 14 about mounting portion 44. Piston member 30 can be grasped and pulled proximally into housing 20 against the distal bias of piston member 30 to allow the implants to be positioned along mounting portion 44. After loading of the implants, actuator 70 is rotated to its first rotational alignment with mounting member 40, where it automatically returns toward the position of FIGS. 5A and 5B to retain the loaded implants on mounting portion 44. Piston member 30 can then be released to contact the proximal most implant 14 along mounting portion 44 and force the distal-most implant 14 into contact with distal retaining member 120*a*.

Further details of the components of delivery instrument 10 are shown in FIG. 7-13. In FIG. 7 mounting member 40 is shown in longitudinal section view. Mounting member 40 includes proximal end member 42 defining a cylindrical receptacle 43 for receiving a proximal portion of actuator 70, as discussed further below. A number of holes can be provided about end member 42 to facilitate longitudinal movement of actuator 70 therein without build-up of resistive air pressure. Mounting member 40 further includes a threaded collar 46 adjacent end member 42, and an elongated tubular portion 48 extending distally from collar 46. Tubular portion 48 defines a passage 49 extending therethrough that opens into the receptacle 43 defined by end member 42 and at the distal end of tubular portion 48.

The distal end of mounting member 40 includes a threaded tip portion 52 for threadingly receiving positioning member 140 thereabout, as shown in FIG. 5B for example. Positioning member 140 includes a proximal internally threaded portion 142 engageable about tip portion 52 and a distally extending locator tip 144. Locator tip 144 includes a reduced diameter or size relative to proximal portion 142 and mounting member 40, and can be positioned in an implant receptacle or other structure at the surgical site to assist in positioning delivery instrument 10 in the desired position and orientation relative to the implantation location. In one embodiment, locator tip 144 is smaller in size than mounting portion 44 to assist in placing delivery instrument 10 in overlapping relation with the implantation location. For example, locator tip 144 can be placed in a tool recess in a proximal end of a bone anchor. The implants can be delivered to the bone anchor without slipping off, fall between or otherwise misaligning with the bone anchor as the implant slides off positioning member 140.

Passage 49 can includes a proximal portion 49*b* and a reduced size distal portion 49*a*. Detents 44*a*, 44*b* are located through the wall of tubular portion 48 in communication with distal passage portion 49a. Actuator 70, shown also in FIGS. 8-10, includes an elongated proximal shaft portion 80 that is received in proximal portion 49b of passage 49 and distal actuating end 74 that is received in distal portion 49a of passage 49. The axial positioning of recesses 76, 78 and shaft actuating portions 75, 77 relative to detents 44a, 44b to effect deployment and recessing of retaining members 120a, 120b is discussed above. Actuating end 74 includes a threaded distal tip 82 for threadingly engaging end cap 130. End cap 130 can abuttingly engage the adjacent distally oriented wall of mounting member 40 to assist in maintaining actuator 70 in the retaining position shown in FIG. 5B.

Proximal user engaging end 72 of actuator 70 includes a gripping portion 84 and a cylindrical portion 86 extending from gripping portion 84 to shaft portion 80. Gripping portion 84 can be tapered in at least one dimension to narrow proximally and can be concavely curved to facilitate gripping by the user to apply the rotational and axial forces to actuator 70. Cylindrical portion 86 is rotatably received in receptacle 43 defined by end member 42 of mounting member 40. Actuator biasing member 100 (FIGS. 1-4) can be a spring positioned about shaft portion 80 and into contact with the distally oriented wall 87 of cylindrical portion 86. Biasing member 100 also contacts a proximally oriented wall 56 in end member 42 to normally bias actuator 70 proximally relative to mounting member 40.

Alignment pin 110 (shown in FIG. 13) includes an outer portion 114 engaged in hole 54 of end member 42 and an inner portion 112 positioned in a keyway in cylindrical portion 86. The keyway is formed by an axial slot portion 86a and a transverse slot portion 86b at the proximal end of axial slot portion 86a. Inner portion 112 is received in axial slot portion 86a when delivery instrument 10 is rotationally aligned in the dispensing orientation. With biasing member 100 normally biasing actuator 70 proximally relative to mounting member 40, alignment pin 110 normally resides at the distal end of axial slot 86a, positioning actuating end 74 and retaining mechanism 120 in mounting member 40 to the retaining position as shown in FIG. 5B.

To advance actuating member 70 and place actuating end 74 and retaining mechanism 120 in the dispensing position as shown in FIG. 5C, user engaging end 72 is depressed against the bias of biasing member 100, and alignment pin 110 moves along axial slot portion 86a to its proximal end. If it is desired to position delivery instrument 10 in the loading orientation, then from the dispensing position gripping portion 84 can be gripped to rotate actuator 70 in mounting member 40, advancing alignment pin 110 into transverse slot portion 86b. When alignment pin 110 has been translated to the end of transverse slot portion 86b opposite axial slot portion 86a, actuator 70 is maintained in the depressed condition against the bias of biasing member 100, and actuating end 74 is maintained in the axial and rotational position shown in FIG. 6B to permit loading of implants about mounting portion 44.

Housing 20 is shown in longitudinal section view in FIG. 11. Housing 20 includes a longitudinal bore 21 extending between and opening through a distal end 22 and a proximal end 24. Proximal end 24 includes internal threads 26 to threadingly engage collar 46 of mounting member 40. Distal end 22 includes an internal lip 28 extending thereabout.

Figure 12:
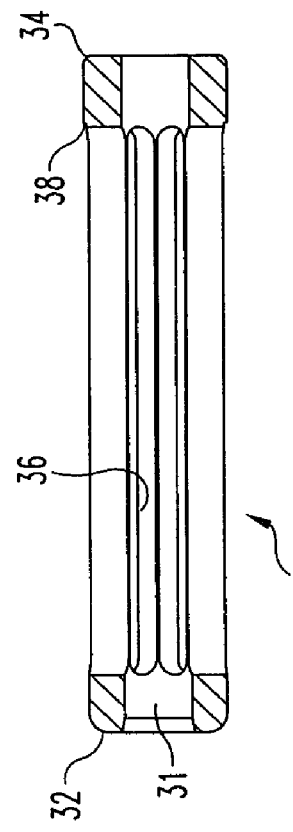
FIG. 12 is a longitudinal section view of a piston member of the delivery instrument of FIG. 1.
Figure 13:
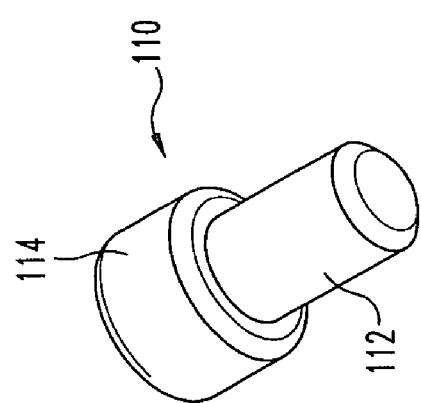
FIG. 13 is a perspective view of an alignment pin of the delivery instrument of FIG. 1.

Piston member 30 is shown in FIG. 12, and includes an elongated body extending between a distal end 32 and a proximal end 34. Piston member 30 includes a central bore 31 sized for positioning about tubular portion 48 of mounting member 40. Piston member 30 can include a number of elongated slots 36 extending therethrough and spaced radially thereabout to facilitate movement of piston member 30 between housing 20 and mounting member 40. Piston biasing member 90 can be in the form of a spring positioned about tubular portion 48 with a distal end of piston biasing member 90 in contact with proximal end 34 of piston member 30, and a proximal end of piston biasing member 90 in contact with collar 46.

Biasing member 90 pushes piston member 30 against the proximal-most implant 14 and forces the distal-most implant 14 into contact with retaining mechanism 120. Piston member 30 further includes an external lip 38 adjacent proximal end 34 that contacts internal lip 28 of housing 20 adjacent the distal end of housing 20. Contact between the lips 28, 38 retains piston member 30 about tubular portion 48 of mounting member 40 even when piston member 30 is fully extended distally from housing 20 under the force of biasing member 90, as shown in FIGS. 1 and 2.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An instrument for delivering multiple implants to at least one surgical location in a patient, comprising:
   a mounting member including an elongate tubular portion extending between a distal mounting portion for receiving multiple implants therealong and a proximal end member;
   a retaining mechanism housed in said mounting portion of said mounting member, said retaining mechanism being movable between a retaining position for retaining the implants along the mounting portion and a dispensing position allowing a distal-most implant on the mounting portion to move distally along the mounting portion for delivery to the at least one surgical location;
   an actuator coupled to said mounting member including a proximal engaging end adjacent said proximal end member of said mounting member, said actuator extending from said proximal engaging end through said tubular portion to an actuating end along said mounting portion, said actuator having a first axial position with said actuating end positioning said retaining mechanism in said retaining position, said actuator being movable in said mounting member to a second axial position with said actuating end positioning said retaining mechanism in said dispensing position;
   a housing having a proximal end mounted to said proximal end member of said mounting member, said housing extending about said tubular portion of said mounting member; and
   a piston member in said housing, said piston member being axially movable about said tubular portion and being biased distally into contact with a proximal most one of the multiple implants about said mounting portion.

2. The instrument of claim 1, wherein:
   said actuating end includes a recess, a distal actuating shaft portion extending distally from said recess, and a proximal actuating shaft portion extending proximally from said recess;
   said retaining mechanism includes a proximal retaining member and a distal retaining member independently movable relative to one another;
   in said retaining position said distal actuating shaft portion contacts said distal retaining member with said distal retaining member projecting outwardly from said mounting portion and said recess aligns with said proximal retaining member to recess said proximal retaining member in said mounting portion; and in said dispensing position said recess aligns with said distal retaining member to recess said distal retaining member in said mounting portion and said proximal actuating shaft portion contacts said proximal retaining member with said proximal retaining member projecting outwardly from said mounting portion.

3. The instrument of claim 2, wherein said actuator includes a first rotational alignment in said mounting member when moving between said first and second axial positions, wherein when in said second axial position said actuator is rotatable about a longitudinal axis thereof to a second rotational alignment in said mounting member, wherein in said second rotational alignment said actuating end includes an elongated recess in said actuating end aligned with each of said proximal and distal retaining members, said elongated recess being configured to recess both of said proximal and distal retaining members in said mounting portion of said mounting member.

4. The instrument of claim 1, wherein said housing includes an internal lip adjacent a distal end thereof and said piston member includes an external lip adjacent a proximal end thereof contactable with said internal lip to limit a distal displacement of said piston member relative to said housing and said mounting member.

5. The instrument of claim 1, wherein said mounting member includes a positioning member at a distal end of said tubular portion thereof, said positioning member including a distally extending tip having a reduced size configuration relative to said tubular portion of said mounting member.

6. An instrument for delivering multiple implants to at least one surgical location in a patient, comprising:

a mounting member including an elongate tubular portion extending between a distal mounting portion for receiving multiple implants therealong and a proximal end member;

an actuator including a distal actuating end in said tubular portion of said mounting member, said actuator extending from said distal actuating end to a proximal engaging end received in said end member of said mounting member, said actuator having a first rotational alignment relative to said mounting member wherein said actuator is axially movable in said mounting member between a retaining position and a dispensing position;

a distal retaining member and a proximal retaining member in said mounting portion in contact with said actuating end of said actuator, wherein:

in said retaining position said distal retaining member projects outwardly from said mounting portion and contacts a distal-most implant to axially retain the multiple implants on the mounting portion and said proximal retaining member is recessed in said mounting portion; and in said dispensing position said distal retaining member is recessed into said mounting portion to permit the distal-most implant to advance distally along said mounting portion for implantation and said proximal retaining member projects outwardly from said mounting portion to contact a second implant proximal of the distal-most implant to axially retain the second implant on said mounting portion, further comprising a biasing member distally biasing the multiple implants into contact with said retaining mechanism and said biasing member includes a piston member positioned about said mounting member and distally biased relative thereto.

7. The instrument of claim 6, wherein said actuator is rotatable from said first rotational alignment when in said dispensing position to a second rotational alignment in said mounting member, wherein in said second rotational alignment said actuating end is structured so that said proximal and distal retaining members are both recessed in said mounting portion of said mounting member.

8. The instrument of claim 6, wherein said actuator is normally biased relative to said mounting member to said retaining position.

9. The instrument of claim 6, wherein said proximal end member of said mounting member includes a proximally opening receptacle and said actuator includes a proximal cylindrical portion received in said proximal end member of said mounting member, and further comprising a spring extending between a proximally facing wall in said proximal end member of said mounting member and a distally facing wall of said proximal cylindrical portion of said actuator, said spring biasing said actuator proximally in said mounting member.

10. An instrument for delivering multiple implants to at least one surgical location in a patient, comprising:

a mounting member including an elongate tubular portion extending between a distal mounting portion for receiving multiple implants therealong and a proximal end member;

an actuator including a distal actuating end in said tubular portion of said mounting member, said actuator extending from said distal actuating end to a proximal engaging end received in said end member of said mounting member, said actuator having a first rotational alignment relative to said mounting member wherein said actuator is axially movable in said mounting member between a retaining position and a dispensing position;

a distal retaining member and a proximal retaining member in said mounting portion in contact with said actuating end of said actuator, wherein:

in said retaining position said distal retaining member projects outwardly from said mounting portion and contacts a distal-most implant to axially retain the multiple implants on the mounting portion and said proximal retaining member is recessed in said mounting portion; and in said dispensing position said distal retaining member is recessed into said mounting portion to permit the distal-most implant to advance distally along said mounting portion for implantation and said proximal retaining member projects outwardly from said mounting portion to contact a second implant proximal of the distal-most implant to axially retain the second implant on said mounting portion, wherein said actuator is rotatable from said first rotational alignment when in said dispensing position to a second rotational alignment in said mounting member, wherein in said second rotational alignment said actuating end is structured so that said proximal and distal retaining members are both recessed in said mounting portion of said mounting member, wherein said actuator includes a proximal end cylinder rotatably received in said proximal end member of said mounting member, said proximal end cylinder including an axially extending slot portion and a transverse slot portion extending partially about said cylinder from a proximal end of said axially extending slot portion, and further comprising an alignment pin with an outer end fixed to said proximal end member and an inner end in said axially extending slot portion as said actuator moves between said retaining and dispensing positions, said inner end of said alignment pin further being received in said transverse slot portion as said actuator is rotated from said first rotational alignment to said second rotational alignment.

11. An instrument for delivering multiple implants to at least one surgical location in a patient, comprising:
- a mounting member including an elongate tubular portion extending between a distal mounting portion for receiving multiple implants therealong and a proximal end member;
- an actuator including a distal actuating end in said tubular portion of said mounting member, said actuator extending from said distal actuating end to a proximal engaging end received in said end member of said mounting member, said actuator having a first rotational alignment relative to said mounting member wherein said actuator is axially movable in said mounting member between a retaining position and a dispensing position;
- a distal retaining member and a proximal retaining member in said mounting portion in contact with said actuating end of said actuator, wherein:
  - in said retaining position said distal retaining member projects outwardly from said mounting portion and contacts a distal-most implant to axially retain the multiple implants on the mounting portion and said proximal retaining member is recessed in said mounting portion; and
  - in said dispensing position said distal retaining member is recessed into said mounting portion to permit the distal-most implant to advance distally along said mounting portion for implantation and said proximal retaining member projects outwardly from said mounting portion to contact a second implant proximal of the distal-most implant to axially retain the second implant on said mounting portion, further comprising:
- a housing having a proximal end secured to said proximal end member of said mounting member, said housing extending about said tubular portion of said mounting member to a distal end; and
- a piston member within said housing and positioned about said tubular portion, said piston member being biased distally along said tubular portion and into contact with a proximal-most implant along said mounting portion.

12. An instrument for delivering multiple implants to at least one surgical location in a patient, comprising:
- a mounting member including an elongate tubular portion extending between a distal mounting portion for receiving multiple implants therealong and a proximal end member;
- an actuator including a distal actuating end in said tubular portion of said mounting member, said actuator extending from said distal actuating end to a proximal engaging end received in said end member of said mounting member, said actuator having a first rotational alignment relative to said mounting member wherein said actuator is axially movable in said mounting member between a retaining position and a dispensing position;
- a distal retaining member and a proximal retaining member in said mounting portion in contact with said actuating end of said actuator, wherein:
  - in said retaining position said distal retaining member projects outwardly from said mounting portion and contacts a distal-most implant to axially retain the multiple implants on the mounting portion and said proximal retaining member is recessed in said mounting portion; and
  - in said dispensing position said distal retaining member is recessed into said mounting portion to permit the distal-most implant to advance distally along said mounting portion for implantation and said proximal retaining member projects outwardly from said mounting portion to contact a second implant proximal of the distal-most implant to axially retain the second implant on said mounting portion,
- wherein said proximal end member of said mounting member includes a proximally opening receptacle and said actuator includes a proximal cylindrical portion received in said proximal end member of said mounting member, and further comprising a spring extending between a proximally facing wall in said proximal end member of said mounting member and a distally facing wall of said proximal cylindrical portion of said actuator, said spring biasing said actuator proximally in said mounting member, further comprising an alignment pin having an outer end fixed in said end member of said mounting member and an inner end contacting said proximal cylindrical portion of said actuator in an axially extending slot to retain said actuator in said mounting member.

13. A surgical system, comprising:
- a delivery instrument including an elongated mounting member having a distal mounting portion and a proximal end member, an actuator in said mounting member including an actuating end in said mounting portion and a proximal engaging end extending proximally from said proximal end member of said mounting member, and a retaining mechanism in said mounting member in contact with said actuating end, said retaining mechanism being movable upon axial displacement of said actuator in said mounting member between a retaining position and a dispensing position; and
- a plurality of implants positioned about said mounting portion of said mounting member, said plurality of implants including a distal-most implant in contact with said retaining mechanism in said retaining position, wherein said plurality of implants include a proximal-most implant in contact with a biasing member biasing the plurality of implants distally into contact with said retaining mechanism, wherein said biasing member includes a piston member positioned about said mounting member and distally biased relative thereto and said delivery instrument includes a housing about said mounting member fixed to said proximal end member of said mounting member, said piston member including a distal end in contact with the proximal-most implant and a proximal end captured in said housing to limit distal movement of said piston relative to said housing and said mounting member.

14. The system of claim 13, wherein the plurality of implants are washers.

* * * * *